(12) United States Patent
Wang et al.

(10) Patent No.: US 11,584,702 B2
(45) Date of Patent: Feb. 21, 2023

(54) PROCESS FOR PRODUCING TRIFLUOROIODOMETHANE (CF3I) FROM TRIFLUOROACETIC ANHYDRIDE (TFAA)

(71) Applicant: Honeywell International Inc., Charlotte, NC (US)

(72) Inventors: Haiyou Wang, Amherst, NY (US); Haridasan K. Nair, Williamsville, NY (US)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 17/540,919

(22) Filed: Dec. 2, 2021

(65) Prior Publication Data

US 2022/0177394 A1 Jun. 9, 2022

Related U.S. Application Data

(60) Provisional application No. 63/122,753, filed on Dec. 8, 2020.

(51) Int. Cl.
*C07C 17/361* (2006.01)
*C07C 17/38* (2006.01)
*B01J 19/12* (2006.01)

(52) U.S. Cl.
CPC ........... *C07C 17/361* (2013.01); *B01J 19/123* (2013.01); *C07C 17/38* (2013.01); *B01J 2219/00033* (2013.01); *B01J 2219/00936* (2013.01)

(58) Field of Classification Search
CPC ...... C07C 17/361; C07C 19/16; B01J 19/123; B01J 2219/00936
See application file for complete search history.

(56) References Cited

U.S. PATENT DOCUMENTS

2006/0122440 A1 6/2006 Mukhopadhyay et al.
2020/0199049 A1 6/2020 Yang et al.

FOREIGN PATENT DOCUMENTS

CN 102992943 A 3/2013

OTHER PUBLICATIONS

Lesniak et al., trifluoroacetic acid and trifluoroacetic anhydride radical cations dissociate near the ionization limit, (The Journal of Physical Chemistry A, 2019, 123, 6313-6318).*
Lin et al., photo-driven redox-neutral decarboxylative carbon-hydrogen trifluoromethylation of arenes with trifluoroacetic acid, (Nature communication, published Feb. 6, 2017 pp. 1-7).*
International Search Report and Written Opinion received for PCT Patent Application No. PCT/US21/072804, dated Apr. 6, 2022, 11 pages.
Lee et al., "Synthesis of CF3I by direct iodination of CF3COOH on solid catalyst," Journal of the Korean Institute of Chemical Engineers, vol. 39, No. 2, Apr. 1, 2001, pp. 144-149.
(Continued)

*Primary Examiner* — Jafar F Parsa
(74) *Attorney, Agent, or Firm* — Faegre Drinker Biddle & Reath LLP

(57) ABSTRACT

The present disclosure relates to a method for producing trifluoroiodomethane ($CF_3I$) from iodine ($I_2$) and trifluoroacetic anhydride (TFAA) under photochemical conditions using ultraviolet (UV) light.

20 Claims, 2 Drawing Sheets

(56) References Cited

OTHER PUBLICATIONS

Lin et al., "Photo-driven redox-neutral decarboxylative carbon-hydrogen trifluoromethylation of (hetero)arenes with trifluoroacetic acid," Nature communication, vol. 8, No. 14353, Feb. 6, 2017, pp. 1-7.

Yin et al., "Photoredox Catalytic Trifluoromethylation and Perfluoroalkylation of Arenes Using Trifluoroacetic and Related Carboxylic Acids," Cell Reports Physical Science, vol. 1, No. 8, Article No. 100141, Aug. 26, 2020, 10 pages.

* cited by examiner

PROCESS FOR PRODUCING TRIFLUOROIODOMETHANE (CF3I) FROM TRIFLUOROACETIC ANHYDRIDE (TFAA)

CROSS-REFERENCE TO RELATED APPLICATIONS

This application claims priority to U.S. Provisional Application No. 63/122,753, filed Dec. 8, 2020, which is herein incorporated by reference in its entirety.

FIELD

The present disclosure relates to a method for producing trifluoroiodomethane ($CF_3I$). More specifically, the present disclosure relates to a method for producing trifluoroiodomethane ($CF_3I$) from iodine ($I_2$) and trifluoroacetic anhydride (TFAA) under photochemical conditions.

BACKGROUND

Trifluoroiodomethane ($CF_3I$) is a useful compound in commercial applications, as a refrigerant or a fire suppression agent, for example. Trifluoroiodomethane is an environmentally acceptable compound with a low global warming potential and low ozone depletion potential. Trifluoroiodomethane ($CF_3I$) can replace more environmentally damaging materials.

Few methods for its preparation are known in the art; for example, trifluoroiodomethane ($CF_3I$) may be prepared from iodine ($I_2$) and various trifluoromethylated materials: $CF_3H$ (see U.S. Pat. No. 7,132,578 and references therein, and Journal of Fluorine Chemistry, 2009, Volume 130, page 231); trifluoroacetic acid (TFA) ($CF_3CO_2H$) (see Hwahak Konghak, 2001, Volume 39 Number 2, pages 144-49); and various trifluoroacetate salts ($CF_3CO_2M$), where M may be sodium, potassium, lithium, silver, copper, etc. (see Journal of the American Chemical Society, 1950, Volume 72, page 3806; Journal of Organic Chemistry, 1967, Volume 32, page 833). U.S. Pat. No. 7,132,587 describes the preparation of trifluoroiodomethane ($CF_3I$) from many other starting materials, such as trifluorochloromethane ($CF_3Cl$), trifluorobromomethane ($CF_3Br$), trifluoromethyltrifluoromethylsilane ($CF_3SiMe_3$), trifluoromethyl ketones ($RCOCF_3$), and trifluoroacetaldehyde ($CF_3CHO$). Hazeldine et. al report the formation of trifluoromethyl iodode ($CF_3I$) as a minor product (15-22%) along with hexafluoroethane ($C_2F_6$) as the major product by passing a nitrogen diluted mixture of trifluoroacetyl chloride ($CF_3COCl$), iodine ($I_2$) and hydrogen iodide (HI) through hot tube at 550° C. to 600° C. for 8 hours (see Journal of the Chemical Society, 1951, pages 584-587). The formation of trifluoroiodomethane ($CF_3I$) was also reported from the reaction of trifluoroacetyl chloride ($CF_3COCl$) and potassium iodide (KI) at 200° C. for 6 hours in an autoclave (see Journal of Organic Chemistry, 1958, Volume 23, page 2016).

The above examples for making trifluoroiodomethane ($CF_3I$) are either difficult to scale up commercially or not cost effective due to poor yields, formation of undesired by-products and expensive raw materials. Thus, there is a need to develop a cost-effective process that can be scaled up to produce commercial quantities of trifluoroiodomethane ($CF_3I$) from relatively inexpensive raw materials.

SUMMARY

The present disclosure provides a method for making trifluoroiodomethane ($CF_3I$) comprising: combining iodine ($I_2$) and trifluoroacetic anhydride (TFAA); and irradiating the mixture with ultraviolet (UV) light to produce a product stream. The combining and irradiating steps may be conducted continuously.

The UV light is may be broad spectrum UV light in the range of 200 nm-400 nm. Alternatively, the UV light may be of a single wavelength, such as 254 nm.

The irradiating step may be conducted with the iodine ($I_2$) and trifluoroacetic anhydride (TFAA) in the liquid phase, or the irradiating step may be conducted with the iodine ($I_2$) and trifluoroacetic anhydride (TFAA) in the gas phase.

The product stream may be purified. One possible purification method comprises passing the product stream through two or more cold traps. One cold trap may be used to remove residual solvent and/or reactants, and possible by-products. A second cold trap may be used to collect the trifluoroiodomethane ($CF_3I$) product.

DETAILED DESCRIPTION

The present disclosure relates to a method for making trifluoroiodomethane ($CF_3I$), by reacting trifluoroacetic anhydride (TFAA) and iodine ($I_2$) as shown below in Equation 1.

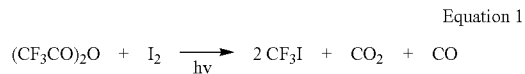

$$(CF_3CO)_2O + I_2 \xrightarrow{h\nu} 2\,CF_3I + CO_2 + CO \quad \text{Equation 1}$$

The reaction may be performed in a continuous fashion by adding a solution of iodine ($I_2$) in a solvent, such as mesitylene, to a reactor along with liquid trifluoroacetic anhydride (TFAA) at a predetermined rate. Alternatively, the iodine ($I_2$) may be neat iodine ($I_2$). The mixture may then be irradiated with ultraviolet (UV) light. The product stream comprises trifluoroiodomethane ($CF_3I$), carbon dioxide ($CO_2$) and carbon monoxide (CO). The solvent, if any, carbon dioxide ($CO_2$), and carbon monoxide (CO) may then be removed by passing the mixture through at least one cold trap.

The present disclosure further provides for a method of making trifluoroiodomethane ($CF_3I$) in which melted iodine ($I_2$) at a temperature of about 120° C. or higher may be combined with trifluoroacetic anhydride (TFAA). This mixture may then be irradiated with ultraviolet (UV) light to form a product stream comprising trifluoroiodomethane ($CF_3I$), carbon dioxide ($CO_2$) and carbon monoxide (CO). These byproducts may be removed by passing the mixture through one or more cold traps. If desired, a solution of iodine ($I_2$) in a solvent, such as mesitylene, xylenes, or toluene, may be used in place of the melted iodine ($I_2$). The products may be analyzed by gas chromatography (GC) and/or gas chromatography-mass spectrometry (GC-MS), for example.

Figure 1:
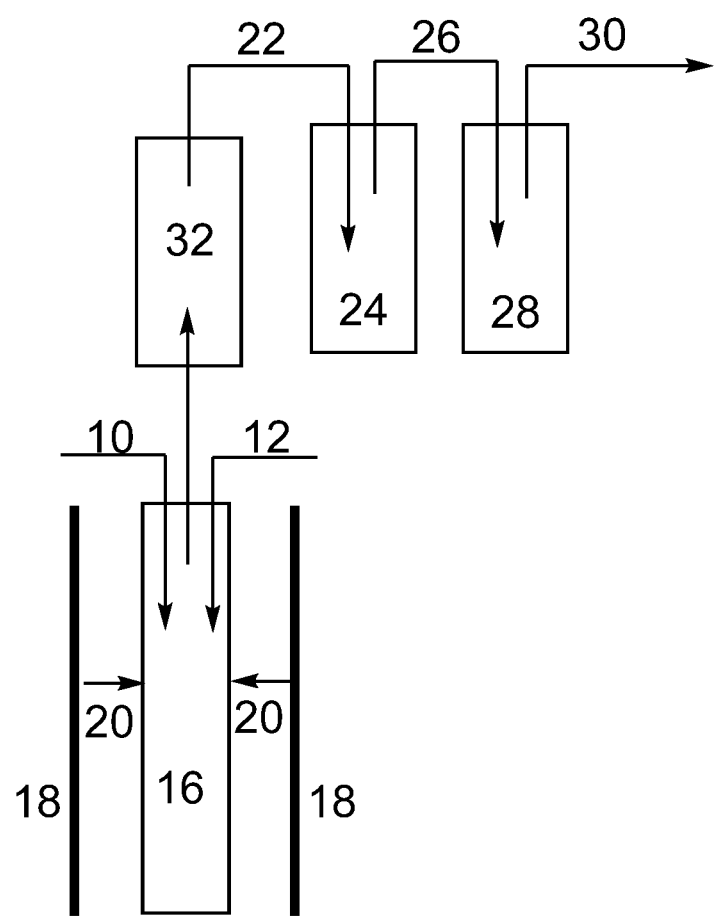
FIG. 1 shows a schematic for a liquid phase continuous process for making trifluoroiodomethane ($CF_3I$) as described in Example 1 and Example 2.

One possible reaction schematic for a liquid phase continuous reaction is shown in FIG. 1. As shown therein, iodine ($I_2$) 10 and trifluoroacetic anhydride (TFAA) 12 may be fed 14 to a quartz tube reactor 16. An ultraviolet (UV) lamp 18 may be used to provide ultraviolet (UV) light 20 to the reaction mixture. A first product stream 22 comprising trifluoroiodomethane ($CF_3I$), carbon dioxide ($CO_2$), carbon monoxide (CO) and any unreacted starting materials may be passed through a condenser 32, then to a first cold trap 24. The first cold trap 24 may be used to capture any unreacted starting materials. From the first cold trap 24, a second product stream 26 comprising trifluoroiodomethane ($CF_3I$), carbon dioxide ($CO_2$), and carbon monoxide (CO) may be passed to a second cold trap 28. The second cold trap 28 may be used to capture trifluoroiodomethane ($CF_3I$), and undesired carbon dioxide ($CO_2$) and carbon monoxide (CO) may be vented 30.

The first product stream may be passed through the condenser to maintain an appropriate solvent level in the reaction. Any appropriate means of agitation may be used in the reaction, such as magnetic stirring, for example.

Figure 2:
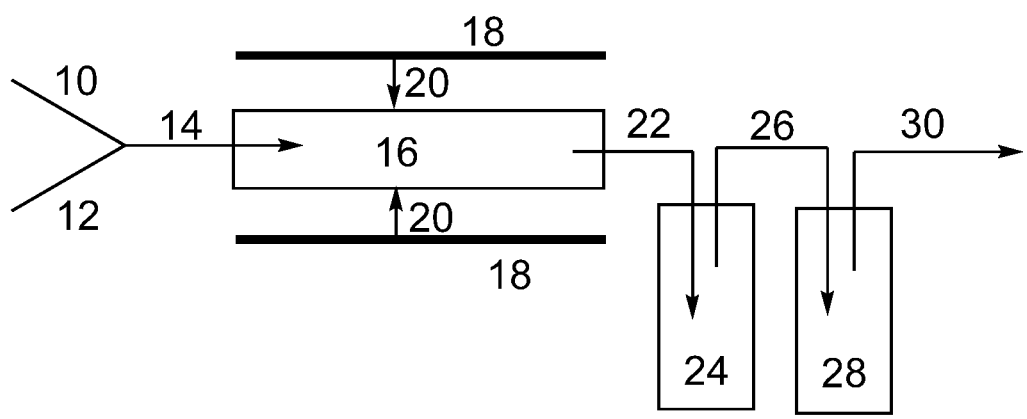
FIG. 2 shows a schematic for a gas phase continuous process for making trifluoroiodomethane ($CF_3I$) as described in Example 3.

Alternatively, a gas phase continuous reaction may be conducted as shown in FIG. 2. As shown therein, iodine ($I_2$) 10 and trifluoroacetic anhydride (TFAA) 12 may be fed 14 to a quartz tube reactor 16. An ultraviolet (UV) lamp 18 may be used to provide ultraviolet (UV) light 20 to the reaction mixture. A first product stream 22 comprising trifluoroiodomethane ($CF_3I$), carbon dioxide ($CO_2$), carbon monoxide (CO) and any unreacted starting materials may be passed to a first cold trap 24. The first cold trap 24 may be used to capture any unreacted starting materials. From the first cold trap 24, a second product stream 26 comprising trifluoroiodomethane ($CF_3I$), carbon dioxide ($CO_2$), and carbon monoxide (CO) may be passed to a second cold trap 28. The second cold trap 28 may be used to capture trifluoroiodomethane ($CF_3I$), and undesired carbon dioxide ($CO_2$) and carbon monoxide (CO) may be vented 30.

A reaction solvent may be used. Suitable solvents are inert under the reaction conditions and are unreactive with the starting materials. Suitable solvents may include mesitylene, toluene, and xylenes, for example.

The ratio of iodine ($I_2$) to trifluoroacetic anhydride (TFAA) may be about 0.1:1, about 5:1, about 10:1, about 20:1, about 30:1, about 40:1, about 50:1, about 60:1, about 70:1, about 80:1, about 90:1, about 100:1, or within any range encompassing these endpoints. Typically, the ratio may be from about 10:1 to about 20:1.

The reaction mixture may be substantially free of water. Specifically, the reaction mixture may contain water in an amount of about 500 ppm or less, about 400 ppm or less, about 250 ppm or less, about 100 ppm or less, or about 50 ppm or less.

The reaction may be conducted under photochemical conditions. Ultraviolet (UV) light may be used in the reaction. The UV light may be broad spectrum or single wavelength. Broad spectrum UV light may be in the 200 nm to 400 nm range. A single wavelength of UV light may be used, at a wavelength which may be as low as about 200 nm, about 250 nm, about 254 nm, about 270 nm, about 280 nm, about 300 nm, as high as about 320 nm, about 350 nm, about 360 nm, about 380 nm, about 400 nm, or within any range encompassing these endpoints.

The reaction may be conducted in a quartz tube reactor. Alternatively, the reaction may be conducted in a photoreactor.

The liquid phase reaction temperature may be about 25° C. or higher, about 40° C. or higher, about 50° C. or higher, about 60° C. or lower, about 75° C. or lower, about 80° C. or lower, about 90° C. or lower, about 100° C. or lower, or within any range encompassing these endpoints, such as from about 60° C. to about 80° C.

Alternatively, the reaction may be conducted in the gas phase in a horizontal quartz reactor. The gas phase reaction temperature may be about 120° C. or higher, about 130° C. or higher, about 140° C. or higher, about 150° C. or higher, about 160° C. or lower, about 170° C. or lower, about 180° C. or lower, about 190° C. or lower, about 200° C. or lower, or within any range encompassing these endpoints.

The reaction pressure was about 0.8 atm or higher, about 1.0 atm or higher, about 1.2 atm or higher, about 1.4 atm or lower, about 1.6 atm or lower, about 1.8 atm or lower, about 2.0 atm or lower, or within any range encompassing these endpoints, such as from about 1.0 atm to about 1.5 atm.

The product stream comprising trifluoroiodomethane ($CF_3I$), carbon dioxide ($CO_2$), carbon monoxide (CO), iodine ($I_2$), trifluoroacetic anhydride (TFAA), and solvent may be sent to two or more cold traps to separate the desired product. A first cold trap may be used to collect any residual iodine ($I_2$) and/or solvent vapor. The temperature of the first cold trap may be about −15° C. or higher, about −10° C. or higher, about −5° C. or lower, about 0° C. or lower, about 5° C. or lower, or within any range encompassing these endpoints.

A second cold trap may be used to collect trifluoroiodomethane ($CF_3I$). The temperature of the second cold trap may be about −90° C. or higher, about −85° C. or higher, about −80° C. or higher, about −78° C. or lower, about −75° C. or lower, about −70° C. or lower, or within any range encompassing these endpoints.

Alternatively, the product stream may be subjected to other suitable purification conditions. For example, the product stream comprising trifluoroiodomethane ($CF_3I$), carbon dioxide ($CO_2$), carbon monoxide (CO), iodine ($I_2$), trifluoroacetic anhydride (TFAA), and solvent may be passed to a desublimator in which unconverted iodine ($I_2$) is condensed and collected for recycling, followed by a product purification system to isolate trifluoroiodomethane ($CF_3I$) as product. The product purification system can consist of one, two, or more distillation columns.

The product stream comprising carbon monoxide (CO), carbon dioxide ($CO_2$), trifluoracetic anhydride (TFAA), and trifluoroiodomethane ($CF_3I$) may be sent to a first column to obtain a first overhead stream comprising carbon monoxide (CO) and carbon dioxide ($CO_2$), and a first bottom stream comprising trifluoroacetic anhydride (TFAA) and trifluoroiodomethane ($CF_3I$). The first bottom stream may then be sent to a second column to obtain a second overhead stream comprising trifluoroiodomethane ($CF_3I$) and a second bottom stream comprising trifluoracetic anhydride (TFAA). Optionally, the second overhead stream may be sent to one or more distillation columns for further purification.

All distillation columns may be operated at a pressure of about 5 psig, about 10 psig, about 25 psig, about 50 psig, about 100 psig, about 150 psig, about 200 psig, about 300 psig, about 400 psig, about 500 psig, or within any range encompassing these endpoints, such as about 25 psig to about 250 psig, or about 50 psig to about 150 psig.

The reaction conversion may be at least 50%, at least 75%, at least 90%, at least 95%, or at least 98%, based on the initial amount of trifluoroacetic anhydride (TFAA).

EXAMPLES

Example 1

Preparation of Trifluoroiodomethane (CF$_3$I) from Trifluoroacetic Anhydride (TFAA) and Iodine (I$_2$) in Solvent

A 200-mL capacity quartz tube was equipped with a connector with inlets connected to a condenser, an inlet tube to supply trifluoroacetic anhydride (TFAA), and a thermal sensor for measuring internal temperature. The reaction temperature may range from 25° C. to 90° C. The tube was charged with 40 g of iodine (12) and 160 g mesitylene. Twenty-one grams of trifluoroacetic anhydride (TFAA) was added over 10 minutes, and the mixture was stirred with a magnetic stir bar while being irradiated with a Rayonet Photochemical reactor at a wavelength of 200-400 nm, such as 254 nm, for about 1 hour. The condenser was attached to 0° C. chiller. The outlet of the condenser was connected to a sampling port and two traps, at 0° C. and at −78° C., respectively, to collect the product trifluoroiodomethane (CF$_3$I). The product stream was collected over a period of 1 hour.

To the stirred solution of iodine (I$_2$) was added liquid trifluoroacetic anhydride (TFAA) via a syringe pump at a rate ensuring a 2- to 10-fold excess of iodine (I$_2$) over the trifluoroacetic anhydride (TFAA). The exit stream was analyzed by gas chromatography (GC) and gas chromatography-mass spectrometry (GC-MS), which indicated the formation trifluoroiodomethane (CF$_3$I) with greater than 95% selectivity.

Example 2

Preparation of Trifluoroiodomethane (CF$_3$I) from Trifluoroacetic Anhydride (TFAA) and Neat Iodine (I$_2$)

To a 200-mL capacity quartz tube photochemical containing 25.4 grams of heated iodine (I$_2$) at about 120° C. to 130° C.) was added 15 grams of trifluoroacetic anhydride (TFAA). The mixture was irradiated by an Ace® photochemical reactor at 254 nm for 45 minutes. The product stream was passed through cold traps, including a cold trap at −78° C., to collect the trifluoroiodomethane (CF$_3$I). The product stream was analyzed (GC-MS, GC) which indicated the formation trifluoroiodomethane (CF$_3$I) with selectivity of greater than 95% and conversion of 80% based on trifluoroacetic anhydride (TFAA).

Example 3

Gas Phase Reaction for the Preparation of Trifluoroiodomethane (CF$_3$I)

Trifluoroacetic anhydride (TFAA) in the gas phase and iodine (I$_2$) in the gas phase were fed to into quartz tube (1-inch diameter by 18-inch length) placed in a horizontal photoreactor with a wavelength of 254 nm. The flow rates were adjusted with appropriate mass flow controllers in a such way that a molar ratio of trifluoroacetic anhydride (TFAA) to iodine (I$_2$) of about 1:1.2 was maintained during the reaction. The temperature of the reaction was about 120° C. to about 200° C., which may be adjusted via heating assembly inside the photoreactor. The contact time was from about 0.1 min to about 5 min. The product stream from the reactor was passed through two cold traps, at 0° C. and −78° C., respectively. Any unreacted starting material (trifluoroacetic anhydride (TFAA) and iodine (I$_2$) were collected mainly in the 0° C. trap. The trifluoroiodomethane (CF$_3$I) was collected in the −78° C. trap. Under these conditions, 40-100% conversion of trifluoroacetic anhydride (TFAA) was achieved, with a selectivity of greater than 95-98%. The reaction may be carried out in a continuous manner.

ASPECTS

Aspect 1 is a method for making trifluoroiodomethane (CF$_3$I) comprising: combining iodine (I$_2$) and trifluoroacetic anhydride (TFAA); and irradiating the mixture with ultraviolet (UV) light to produce a product stream.

Aspect 2 is the method of Aspect 1, wherein the combining and irradiating steps are conducted continuously.

Aspect 3 is the method of Aspect 1 or Aspect 2, wherein the ratio of iodine (I$_2$) to trifluoroacetic anhydride (TFAA) is from about 0.1:1 to about 100:1.

Aspect 4 is the method of Aspect 3, wherein the ratio of iodine (I$_2$) to trifluoroacetic anhydride (TFAA) is from about 10:1 to about 20:1

Aspect 5 is the method of Aspect 1 or Aspect 2, wherein the ultraviolet (UV) light is broad spectrum ultraviolet (UV) light.

Aspect 6 is the method of Aspect 5, wherein the broad spectrum ultraviolet light (UV) is 200 nm-400 nm ultraviolet (UV) light.

Aspect 7 is the method of Aspect 1 or Aspect 2, wherein the ultraviolet (UV) light is single wavelength ultraviolet (UV) light.

Aspect 8 is the method of Aspect 7, wherein the ultraviolet (UV) light is 254 nm ultraviolet (UV) light.

Aspect 9 is the method of any of Aspects 1-8, wherein the irradiating step is conducted with the iodine (I$_2$) and trifluoroacetic anhydride (TFAA) in the liquid phase.

Aspect 10 is the method of any of Aspects 1-9, further comprising, prior to the combining step, dissolving the iodine (I$_2$) in a solvent.

Aspect 11 is the method of Aspect 10, wherein the solvent is chosen from the group consisting of mesitylene, toluene, and xylenes.

Aspect 12 is the method of any of Aspects 1-11, further comprising purifying the product stream.

Aspect 13 is the method of any of Aspects 1-12, wherein the product stream may be passed through two or more cold traps.

Aspect 14 is the method of Aspect 13, wherein the product stream may be passed through a first cold trap at 0° C.

Aspect 15 is the method of Aspect 13 or Aspect 14, wherein the product stream may be passed through a second cold trap at −78° C.

Aspect 16 is the method of any of Aspects 1-8, wherein the irradiating step is conducted with the iodine (I$_2$) and the trifluoroacetic anhydride (TFAA) in the gas phase.

Aspect 17 is the method of Aspect 16, wherein the product stream may be passed through two or more cold traps.

Aspect 18 is the method of Aspect 17, wherein the product stream may be passed through a first cold trap at 0° C.

Aspect 19 is the method of Aspect 17 or Aspect 18, wherein the product stream may be passed through a second cold trap at −78° C.

What is claimed is:
1. A method for making trifluoroiodomethane (CF$_3$I) comprising:

combining iodine ($I_2$) and trifluoroacetic anhydride (TFAA); and irradiating the mixture with ultraviolet (UV) light to produce a product stream.

2. The method of claim 1, wherein the combining and irradiating steps are conducted continuously.

3. The method of claim 1, wherein the ratio of iodine ($I_2$) to trifluoroacetic anhydride (TFAA) is from about 0.1:1 to about 100:1.

4. The method of claim 3, wherein the ratio of iodine ($I_2$) to trifluoroacetic anhydride (TFAA) is from about 10:1 to about 20:1.

5. The method of claim 1, wherein the ultraviolet (UV) light is broad spectrum ultraviolet (UV) light.

6. The method of claim 5, wherein the broad spectrum ultraviolet light (UV) is 200 nm-400 nm ultraviolet (UV) light.

7. The method of claim 1, wherein the ultraviolet (UV) light is single wavelength ultraviolet (UV) light.

8. The method of claim 7, wherein the ultraviolet (UV) light is 254 nm ultraviolet (UV) light.

9. The method of claim 1, wherein the irradiating step is conducted with the iodine ($I_2$) and trifluoroacetic anhydride (TFAA) in the liquid phase.

10. The method of claim 1, further comprising, prior to the combining step, dissolving the iodine ($I_2$) in a solvent.

11. The method of claim 10, wherein the solvent is chosen from the group consisting of mesitylene, toluene, and xylenes.

12. The method of claim 1, further comprising purifying the product stream.

13. The method of claim 1, wherein the product stream may be passed through two or more cold traps.

14. The method of claim 13, wherein the product stream may be passed through a first cold trap at 0° C.

15. The method of claim 13, wherein the product stream may be passed through a second cold trap at −78° C.

16. The method of claim 1, wherein the irradiating step is conducted with the iodine ($I_2$) and the trifluoroacetic anhydride (TFAA) in the gas phase.

17. The method of claim 16, wherein the product stream may be passed through two or more cold traps.

18. The method of claim 17, wherein the product stream may be passed through a first cold trap at 0° C.

19. The method of claim 17, wherein the product stream may be passed through a second cold trap at −78° C.

20. The method of claim 1, wherein the method achieves a conversion of at least 75%, based on the initial amount of trifluoroacetic anhydride (TFAA).

* * * * *